(12) United States Patent
Pfeffinger et al.

(10) Patent No.: US 8,987,517 B2
(45) Date of Patent: Mar. 24, 2015

(54) PROCESS FOR PREPARING CYCLOALIPHATIC AMINES

(75) Inventors: Joachim Pfeffinger, Ludwigshafen (DE); Willi Doell, Beindersheim (DE)

(73) Assignee: BASF SE, Ludwigshafen (DE)

( * ) Notice: Subject to any disclaimer, the term of this patent is extended or adjusted under 35 U.S.C. 154(b) by 639 days.

(21) Appl. No.: 12/863,137

(22) PCT Filed: Jan. 14, 2009

(86) PCT No.: PCT/EP2009/050341
§ 371 (c)(1),
(2), (4) Date: Jul. 15, 2010

(87) PCT Pub. No.: WO2009/090179
PCT Pub. Date: Jul. 23, 2009

(65) Prior Publication Data
US 2010/0292510 A1    Nov. 18, 2010

(30) Foreign Application Priority Data
Jan. 18, 2008   (EP) ..................................... 08150395

(51) Int. Cl.
*C07C 211/35*  (2006.01)
*C07C 211/36*  (2006.01)
*C08K 5/14*    (2006.01)
*C07C 209/72*  (2006.01)
*C07C 211/44*  (2006.01)

(52) U.S. Cl.
CPC ................. *C08K 5/14* (2013.01); *C07C 209/72* (2013.01); *C07C 211/44* (2013.01); *C07C 2101/14* (2013.01)
USPC ........................................ 564/450; 564/451

(58) Field of Classification Search
CPC .... C07C 211/44; C07C 211/36; C07C 211/35
USPC .................................. 564/450, 451
See application file for complete search history.

(56) References Cited

U.S. PATENT DOCUMENTS

| | | | | |
|---|---|---|---|---|
| 3,864,361 A | * | 2/1975 | Stillman et al. | ............... 548/579 |
| 5,077,032 A | * | 12/1991 | Mizukami et al. | ........... 423/628 |
| 5,214,212 A | * | 5/1993 | Whitman | ..................... 564/451 |
| 5,773,657 A | * | 6/1998 | Rutter et al. | .................. 564/450 |
| 6,504,060 B1 | * | 1/2003 | Bunnenberg et al. | ......... 564/451 |
| 2006/0079717 A1 | * | 4/2006 | Stochniol et al. | ............. 564/450 |
| 2006/0128554 A1 | * | 6/2006 | Kimble et al. | .................. 502/64 |

FOREIGN PATENT DOCUMENTS

| | | |
|---|---|---|
| DE | 44 04 220 A1 | 8/1995 |
| DE | 195 33 718 A1 | 3/1997 |
| EP | 1 251 119 A2 | 10/2002 |
| EP | 1 369 447 A1 | 12/2003 |

OTHER PUBLICATIONS

Barkdoll et al. J. Am. Chem. Soc. 1953, 75, 1156-1159.*
Entry for Inorganic Chemistry, Hawley's Condensed Chemical Dictionary, 14th Edition, 2002.*
Sasol, Puralox/Catalox High purity activated aluminas, 2005.*
Carswell et al., "Cyclohexylamine & Dicyclohexylamine: Properties and Uses," 29 *Indus. & Engineering Chem.* 1247-51 (1937).

* cited by examiner

*Primary Examiner* — Joseph Kosack
*Assistant Examiner* — Matthew Coughlin
(74) *Attorney, Agent, or Firm* — Drinker Biddle & Reath LLP

(57) ABSTRACT

A process for preparing cycloaliphatic amines by hydrogenating the corresponding aromatic compounds with hydrogen-comprising gas at a temperature of from 30 to 280° C. and a pressure of 50-350 bar, in the presence of ruthenium catalysts. The hydrogenation is performed in the presence of from 1% by weight to 500% by weight, based on the catalyst calculated as elemental ruthenium (Ru), of suspended inorganic additives, and to the use of the cycloaliphatic amines as a synthesis unit.

21 Claims, No Drawings

PROCESS FOR PREPARING CYCLOALIPHATIC AMINES

CROSS-REFERENCE TO RELATED APPLICATIONS

This application is a national stage application (under 35 U.S.C. §371) of PCT/EP2009/050341, filed Jan. 19, 2009, which claims benefit of European application 08150395.5, filed Jan. 18, 2008.

FIELD OF THE INVENTION

The present invention relates to a process for preparing cycloaliphatic amines by hydrogenating the corresponding aromatic compounds in the presence of ruthenium (Ru)-comprising catalysts, in the presence of suspended inorganic additives. The present invention further relates to the use of the cycloaliphatic amines thus obtainable.

BACKGROUND OF THE INVENTION

U.S. Pat. No. 2,606,925 describes the hydrogenation of aromatic compounds which are substituted directly on the aromatic ring via nitrogen atoms (for example aromatic amines or nitro compounds) to the corresponding cycloaliphatic compounds. The catalysts used are elemental ruthenium metal, ruthenium oxides, ruthenium salts, ruthenium sulfides and ruthenium sulfates. Optimal results can be achieved according to this document when the ruthenium is present in finely distributed form. However, no method of preparing these catalysts is described.

In U.S. Pat. No. 2,494,563, finely divided Ru catalysts are used for the hydrogenation of aromatic diamines to the corresponding aliphatic diamines.

A method for preparing very small ruthenium dioxide particles by reacting $RuCl_3$ solution with NaOH in the aqueous phase, washing and drying is described in CA-A-860855. This affords crystal sizes less than 50 nm. A preferred use specified for the powder obtained was the production of electrical resistors.

DE-A-2132547 discloses a process for hydrogenating aromatic compounds to the corresponding cycloaliphatic. For the hydrogenation, a catalyst based on oxide hydrates of Ru is used. The catalyst is prepared by precipitation from an aqueous solution of a ruthenium salt by addition of alkali metal hydroxide solution. The ruthenium oxide hydrate thus obtained can be used directly in the process or be subjected to drying before use. After the drying, the catalyst, according to the disclosure, is present in the form of powder with particle sizes in the range from 4 to 6 nm, the Ru being present in the resulting dry powder as Ru(IV) oxide hydrate with approx. 50% by weight of Ru.

DE 101 19 135 A1 describes the continuous preparation of bis(4-aminocyclohexyl)methane by hydrogenation of bis(4-aminophenyl)methane with the aid of a pulverulent ruthenium catalyst. The ruthenium was used applied to an inert support material, e.g. $Al_2O_3$, and with a particle size of 5-150 µm.

U.S. Pat. No. 5,214,212 teaches the addition of metal salts as promoters in a process for hydrogenating aromatic amines. According to the disclosure, the addition of promoters leads to an improvement in the reaction rate and to a reduction in by-product formation. The metal salts were used in concentrations of from 0.3% to 10% based on the aromatic amine.

U.S. Pat. No. 3,864,361 describes the preparation of 2,5-dimethylpyrrolidone by reduction of 2,5-dimethylpyrrole in the presence of finely divided, unsupported $RuO_2$. After the hydrogenation has ended, the catalyst is removed by filtration. According to the disclosure, the removal of the Ru catalyst can be improved by the addition of $Al_2O_3$ as a filtering aid.

The prior art teaches the use of heterogeneous Ru catalysts with small particle sizes, which should be present in very fine distribution in the reaction mixture. When such catalysts are used in an industrial scale process, however, it is found that the small catalyst particles form relatively large agglomerates during the hydrogenation, which can then settle out in the reactor. This firstly removes a portion of the amount of catalyst from the process; secondly, the resulting deposits can cause blockages which lead to disruption in the course of operation.

In the aromatic starting materials which are used in the process for preparing cycloaliphatic amines, there are typically small amounts of by-products which generally cannot be removed quantitatively during the purification of the starting materials. These by-products can poison the ruthenium catalyst and hence reduce the space-time yield of the process.

In the case of the hydrogenation of bis(4-aminophenyl)methane or bis(4-amino-3-methylphenyl)methane to the particular cyclohexyl derivatives, these by-products are principally the hydrochlorides of the aromatic starting amines and higher-boiling aromatic products.

Even when the chlorine content of the particular starting materials is higher than 1 ppm or the concentration of higher-boiling products exceeds the value of 2% by weight, considerable losses in the space-time yield can arise.

BRIEF SUMMARY OF THE INVENTION

It was therefore an object of the present invention to provide a process for preparing cycloaliphatic compounds which has a high space-time yield. In addition, the intention was to develop a process which ensures stable industrial scale operation and reduces the problems which occur through agglomeration of catalyst particles and the resulting blockages. Furthermore, with the aid of the process according to the invention, the yield of product shall be increased and the formation of by-products reduced, especially in the case of use of starting materials which comprise a certain degree of troublesome by-products. Thus, the intention was to ensure stable production operation overall, and a high yield and selectivity.

According to the invention, the object is achieved by a process for preparing cycloaliphatic amines by hydrogenating the corresponding aromatic compounds with hydrogen-comprising gas at a temperature of from 30 to 280° C. and a pressure of 50-350 bar, in the presence of ruthenium catalysts, which comprises performing the hydrogenation in the presence of from 1% by weight to 500% by weight, based on the catalyst (calculated as elemental ruthenium), of suspended inorganic additives.

DETAILED DESCRIPTION OF THE PREFERRED EMBODIMENTS

In the process according to the invention, aromatic compounds which can be hydrogenated to cycloaliphatic amines are used.

Aromatic compounds which can be hydrogenated to cycloaliphatic amines are typically mono- or polycyclic aromatic compounds which comprise one or more nitrogen-containing substituents.

In a preferred embodiment, aromatic compounds with one or more nitrogen-containing substituents are used, in which the nitrogen atom of the nitrogen-containing substituent is bonded directly on the aromatic ring (N-substituted aromatic compounds).

Preference is given to using aromatic mono-, di- or polyamines which can be hydrogenated to the corresponding cycloaliphatic amines.

Useful aromatic amines include mono- or polycyclic aromatic compounds with one or more amine groups, for example:
aromatic monoamines such as aniline, the isomeric toluidines, the isomeric xylidines, 1- or 2-aminonaphthalene, benzidine and substituted benzidines;
aromatic diamines such as the isomeric phenylenediamines, the isomeric tolylenediamines, the isomeric diaminonaphthalenes, 4,4'-diamino-3,3'-dimethyldiphenylmethane, 4,4'-diamino-3,3',5,5'-tetramethyldiphenylmethane and 4,4'-diaminodiphenylmethane; or
aromatic polyamines such as polymeric MDA (polymethylenepolyphenylamine).

The aromatic compounds which can be hydrogenated to cycloaliphatic amines and which are used may also be aromatics with nitro, nitrile and urethane groups as substituents on the aromatic ring,
for example
aromatic compounds with nitro groups as substituents, such as nitrobenzene, nitrotoluene, dinitrobenzene, dinitrotoluene and the isomeric nitroanilines;
aromatic compounds with nitrile groups as substituents, such as benzonitrile, tolunitrile or o-aminobenzonitrile; or
aromatic compounds with urethane groups as substituents, such as the dialkylurethanes which are formed from diphenylmethane 4,4'-diisocyanate, diphenylmethane 2,4'-diisocyanate or diphenylmethane 2,2'-diisocyanate, and aliphatic alcohols such as $C_1$-$C_6$-alcohols, especially n-butanol,
the dialkylurethanes which are formed from tolylene 2,4-diisocyanate or tolylene 2,6-diisocyanate, and aliphatic alcohols such as $C_1$-$C_6$-alcohols, especially n-butanol,
the dialkylurethanes which are formed from polymeric diphenylmethane diisocyanate and aliphatic alcohols such as $C_1$-$C_6$-alcohols, especially n-butanol,
the dialkylurethanes which are formed from phenylene 2,4-diisocyanate or phenylene 2,6-diisocyanate, and aliphatic alcohols such as $C_1$-$C_6$-alcohols, especially n-butanol, or
the dialkylurethanes which are formed from naphthylene 1,5-diisocyanate and aliphatic alcohols such as $C_1$-$C_6$-alcohols, especially n-butanol.

In addition to the substituents which can be hydrogenated to amine groups, the aromatic compounds may have no further substituents or they may bear one or more further substituents, for example alkyl, cycloalkyl, aryl, heteroaryl, halogen, haloalkyl, silyl, hydroxyl, alkoxy, aryloxy, carboxyl or alkoxycarbonyl substituents.

Preference is given to using, in the process, aromatic amines such as the aforementioned aromatic mono-, di- and/or polyamines.

Particular preference is given to using polymeric MDA, aniline, 2,4-diaminotoluene, 2,6-diaminotoluene, o-phenylenediamine, m-phenylenediamine, p-phenylenediamine, 4,4'-diamino-3,3'-dimethyldiphenylmethane, 4,4'-diamino-3,3',5,5'-tetramethyldiphenylmethane and/or 4,4'-diaminodiphenylmethane in the process.

Very particular preference is given to using aniline, 4,4'-diamino-3,3'-dimethyldiphenylmethane, 4,4'-diamino-3,3',5,5'-tetramethyldiphenylmethane and/or 4,4'-diaminodiphenylmethane.

In a particular embodiment, aromatic compounds which can be hydrogenated to the corresponding cycloaliphatic amines which comprise by-products are used in the process according to the invention. Examples of such by-products are hydrochlorides of the aromatic starting amines or higher-boiling aromatic by-products. Higher-boiling by-products refer to those constituents which have a higher boiling point than the aromatic starting compounds which are to be hydrogenated to the cycloaliphatic products.

The chlorine content of the aromatic compounds which can be hydrogenated to the corresponding cycloaliphatic amines is preferably 1 ppm or more, preferably from 10 ppm to 10 000 ppm and more preferably from 20 ppm to 1000 ppm, the chlorine content being determined typically to DIN V 51408 part 2.

The content of higher-boiling aromatic compounds in the starting compounds is generally 1% by weight and more, preferably from 2 to 20% by weight and more preferably from 2 to 10% by weight, the content of higher-boiling aromatic compounds being determined by laboratory distillation to ASTM D 5236-03 at a pressure of 1 mbar and a temperature up to 260° C.

In the process according to the invention, a hydrogen-comprising gas is used. The hydrogen is generally used in technical-grade purity. The hydrogen can also be used in the form of a hydrogen-comprising gas, i.e. in admixtures with other inert gases, such as nitrogen, helium, neon, argon or carbon dioxide. The hydrogen-comprising gases used may, for example, be reformer offgases, refinery gases, etc., when and if these gases do not comprise any catalyst poisons for the Ru catalysts, for example CO. However, preference is given to using pure hydrogen or essentially pure hydrogen in the process.

The aromatic amines are prepared in the presence of Ru catalysts.

In the process according to the invention for hydrogenating aromatic compounds, a heterogeneous Ru catalyst is general used.

The Ru catalyst used in the process may have different morphologies.

For instance, Ru catalysts may comprise support materials.

The support materials used are typically carbon, such as graphite, carbon black and/or activated carbon, aluminum oxide, silicon dioxide, zirconium dioxide, zeolites, aluminosilicates, etc., and also mixtures of these support materials.

Supported catalysts can be prepared by known processes, such as impregnation (described, for example, in A. B. Stiles, Catalyst Manufacture—Laboratory and Commercial Preparations, Marcel Dekker, New York, 1983) or precipitation (described, for example in EP-A2-1106 600, page 4, and A. B. Stiles, Catalyst Manufacture, Marcel Dekker, Inc., 1983, page 15).

The shape and size of the support material may vary. Typical mean particle sizes of support materials are within the range from 0.001 up to 5 millimeters, preferably from 0.0005 to 1 mm, more preferably from 0.001 to 0.5 mm.

The Ru catalyst can also be used without support material; for example, Ru can be used in the form of $RuO_2$ or oxide hydrates of ruthenium. Typically, the mean particle size of heterogeneous Ru catalysts which have been obtained by precipitation is in the range from 1 nm to 1 μm, preferably in the range from 3 nm to 100 nm. For example, the mean particle size of the ruthenium particles which are used in the form of the oxide hydrates of Ru, according to the disclosure of DE-A-2132546, is between 4 and 6 nm.

The heterogeneous Ru catalyst used is preferably a catalyst based on ruthenium oxide hydrate.

Particular preference is given to using an Ru catalyst as disclosed in DE-A-2132547. The preparation of such preferred catalysts is described in detail, for example on pages 4 and 5 and in example 1 of DE-A-2132547.

The Ru catalysts are typically used in suspended form.

The process according to the invention is performed in the presence of inorganic additives.

The specific surface area of the inorganic additives, measured on the basis of ISO 5794-1, annex D, is typically in the range from 10 to 1000 m$^2$/g. Preference is given to substances which have a surface area in the range from 20 to 600 m$^2$/g, more preferably in the range from 25 to 300 m$^2$/g.

The mean primary particle size of the inorganic additives is generally in the range from 1 to 500 nm, preferably from 5 to 200 nm and more preferably from 5 to 100 nm, and is typically determined by means of electron microscopy, for example SEM.

The particle size (d50) of the inorganic additives (laser diffraction based on ISO 13320-1) is typically from 1 to 200 μm.

The tamped density of the inorganic additives (measured on the basis of ISO 787-11) is typically in the range from 10 to 2000 g/l, preferably in the range from 50 to 1000 g/l and more preferably in the range from 50 to 500 g/l.

The inorganic additives are used in suspended form in the process according to the invention.

The inorganic additives used in the process according to the invention may, for example, be inorganic additives selected from the group consisting of aluminum oxide, silicon dioxide, alkali metal, alkaline earth metal and aluminum silicates, alkali metal, alkaline earth metal and aluminum borosilicates, titanium dioxide, metal soaps, zeolites, magnesium oxide, zinc oxide, zirconium oxide and inorganic carbon compounds.

The inorganic additive used may be aluminum oxide, for example α-aluminum oxide or γ-aluminum oxide. Particular preference is given to using γ-aluminum oxide.

The specific surface area of γ-aluminum oxide is generally in the range from 150 to 400 m$^2$/g (cf. Ullmanns Enzyklopädie der Technischen Chemie, 4th edition, volume 7, p. 293 ff).

The inorganic additive used may also be silicon dioxide.

Examples of silicon dioxide which can be used in the process according to the invention are kieselguhr or particular forms of silicas (cf. Ullmanns Enzyklopädie der Technischen Chemie, 4th edition, volume 21, p. 439 ff).

Kieselguhr refers typically to diatomaceous earth (diatomite), which has formed from sedimented diatoms. Processed kieselguhr generally has a specific surface area of from 10 to 25 m$^2$/g.

The silicas generally differ by the method of their production. Examples of silicas are fumed silicas, precipitated silicas and chemically aftertreated silicas.

The term "fumed silicas" generally encompasses the high-dispersity silicas which are obtained from the gas phase by coagulation at high temperatures.

Precipitated silicas are generally obtained by precipitation from an aqueous waterglass solution by means of acid (usually sulfuric acid), subsequent removal of the precipitate and the drying or spray-drying thereof.

Chemically aftertreated silicas are typically understood to mean fumed silicas or precipitated silicas whose surface has been chemically modified by reaction, for example, with chlorosilanes or silicone acids. Examples of fumed or precipitated silicas are the "Sipernat® D17" and "Sipernat® 22" product types from Evonik-Degussa GmbH.

According to the preparation process, the specific surface area of the silicas mentioned is in the range from 10 to 1000 m$^2$/g. Their primary particle size is from approx. 5 to 500 nm. Typical silicas which can be used as additives have, for example, the following values:

| | Specific surface area m$^2$/g | Mean primary particle size nm | Tamped density ISO 787-11 g/l |
|---|---|---|---|
| Fumed silicas | 25-600 | 5-500 | 50-200 |
| Precipitated silicas | 30-1000 | 3-100 | 50-1000 |
| Chem. aftertreated silicas | approx. 110 | approx. 28 | approx. 80 |

The inorganic additives used may also be alkali metal, alkaline earth metal and aluminum silicates. It is possible here to use either naturally occurring or synthetic silicates.

In particular, aluminum silicates include the clay minerals bentonite, fuller's earth, bole, umbra, alumina, montmorillonite, vermiculite or kaolin. These naturally occurring products in some cases comprise minor amounts of further metal constituents, for example iron (cf. Ullmanns Enzyklopädie der Technischen Chemie, 4th edition, volume 23, p. 311 ff.).

It is also possible for calcium silicates or sodium aluminum silicates to find use as inorganic additives. The specific surface area of these silicates is generally from 20 to 200 m$^2$/g. A preferred synthetic sodium aluminum silicate is especially the "Sipernat® 820A" type (from Evonik-Degussa GmbH) with a specific surface area of 85 m$^2$/g and a d50 particle size of 7.5 μm.

Inorganic additives also include alkali metal, alkaline earth metal and aluminum borosilicates. In the borosilicates, the SiO$_4$ tetrahedra which are the basis units of the silicates are partly replaced by BO$_4$ tetrahedra. Examples of borosilicates are tourmaline, alumina-tourmaline or magnesia-alumina-tourmaline. The values of the specific surface area and primary particle size are similar to the values as have been specified for the silicates.

The inorganic additive used may also be titanium dioxide. Titanium dioxide may be present, for example, in the anatase or the rutile polymorph. Preference is given to using titanium dioxide in the anatase polymorph.

The specific surface area of titanium dioxide is typically from approx. 30 to 70 m$^2$/g, the primary particle size is generally between approx. 20 and 40 nm, and the tamped density is generally in the range from 120 to 170 g/l.

Metal soaps may likewise be used as inorganic additives in the process according to the invention.

Examples of metal soaps are the aluminum, cadmium, lithium, calcium, magnesium or zinc salts of fatty acids such as myristic acid, palmitic acid or stearic acid. The particle size of the metal salts is generally less than 200 μm, preferably less than 100 μm.

It is also possible to use naturally occurring or synthetic zeolites as inorganic additives in the process according to the invention. The specific surface area of the zeolites is in many cases 800 m$^2$/g or higher. The size of the synthetic zeolite particles is generally in the range from 1 to 100 μm.

Further suitable additives include magnesium oxide, zinc oxide and zirconium oxide.

The inorganic additives used in the process according to the invention may also be inorganic carbon compounds. Inorganic carbon compounds are, for example, activated carbons, carbon molecular sieves, and natural or synthetic carbon black. The specific surface area of these carbon compounds is, according to the type and production process, typically in the range of 800-1000 $m^2/g$ for activated carbons, generally <100 $m^2/g$ for carbon molecular sieves, and typically <400 $m^2/g$ for carbon black.

Preference is given to using, as inorganic additives, aluminum oxide, silicon dioxide, alkali metal, alkaline earth metal and aluminum silicates, alkali metal, alkaline earth metal and aluminum borosilicates, titanium dioxide, metal soaps, zeolites, magnesium oxide, zinc oxide, zirconium oxide or inorganic carbon compounds.

Particular preference is given to using, as inorganic additives, silicon dioxide, alkali metal, alkaline earth metal and aluminum silicates, alkali metal, alkaline earth metal and aluminum borosilicates, titanium dioxide, metal soaps, zeolites, magnesium oxide, zinc oxide, zirconium oxide or inorganic carbon compounds.

Very particular preference is given to using, as inorganic additives, silicon dioxide, alkali metal, alkaline earth metal and aluminum silicates or alkali metal, alkaline earth metal and aluminum borosilicates.

Special preference is given to using silicon dioxide in the process according to the invention.

The additives mentioned are, as stated above, all known and for the most part commercially available. They typically find use as filtering aids, adsorption materials, as a support material for catalysts or as catalysts.

According to the invention, the inorganic additives are added in an amount of from 1% by weight to 500% by weight, based on the catalyst (calculated as elemental ruthenium). Preference is given to using from 5 to 200% by weight and especially from 20 to 120% by weight of inorganic additives, based in each case on the catalyst (calculated as elemental ruthenium). However, it is also possible to use greater amounts of inorganic additives, though employment of very high amounts may cause blockages owing to the additives.

The amount of the heterogeneous Ru catalysts used in the abovementioned processes is typically within a range of from 0.0005 to 5% by weight of ruthenium, calculated as the metal, based on the substance to be converted, especially on the starting substance to be hydrogenated. The amount of the Ru catalysts used is preferably in the range from 0.001 to 1% by weight of ruthenium based on the substance to be converted, especially on the starting substance to be hydrogenated. The amount of the Ru catalysts used is more preferably in the range from 0.001 to 0.1% by weight of ruthenium based on the substance to be converted.

The hydrogenation can be carried out batchwise or continuously.

In the batchwise reaction regime, the hydrogenation can be carried out, for example, in a stirred tank or stirred autoclave, a loop reactor, a jet loop reactor, a bubble column or a reactor with a pumped circulation system. Preference is given to performing the batchwise hydrogenation in a stirred tank or stirred autoclave.

In the continuous reaction regime, the hydrogenation is typically performed in a continuous stirred tank reactor, a continuous loop reactor, a continuous jet loop reactor, a continuous bubble column or a continuous reactor with a pumped circulation system or a stirred tank cascade.

The process according to the invention is performed at a pressure of 50-350 bar; preference is given to employing a pressure of from 150 to 250 bar.

According to the invention, the process is performed at a temperature in the range between 30 and 280° C., particular preference being given to the temperature range from 120 to 260° C.

The hydrogenation can be carried out with or without solvent. The solvents used are alcohols such as isopropanol, isobutanol or t-butanol, or ethers such as diethyl ether, glycol dimethyl ether, dioxane or tetrahydrofuran.

However, the solvent used may also be the end product formed in the reaction.

Useful solvents also include mixtures of the aforementioned solvents.

Preferred solvents are isopropanol, isobutanol and/or t-butanol. Particular preference is given to using, as the solvent, the end product formed in the reaction.

The solvent is usually employed in such an amount as to obtain from 10 to 50% (% by weight), preferably from 15 to 40% and more preferably from 20 to 30% solutions of the aromatic compounds intended for hydrogenation.

It is particularly advantageous for the continuous performance of the process to employ the end product formed in the reaction as the solvent.

The Ru catalyst and the inorganic additive are used in the form of a suspension of the catalyst and of the additive in the liquid reactants and/or solvents used.

In batchwise mode, the Ru catalyst is typically, either in the form of dry powder or in the form of water-moist filtercake, added directly to the hydrogenation reactor together with the inorganic additive.

Particularly advantageously, the Ru catalyst together with the inorganic additive is mixed with a solvent, the liquid feedstock or liquid reaction effluent to give a suspension which can then be fed to the reactor by means of suitable metering pumps. In continuous mode, this catalyst suspension is typically fed continuously to the hydrogenation reactor.

Some inorganic additives, for example kieselguhr or precipitated silicas, may also already be present in the course of precipitation of the Ru(IV) oxide hydrate particles, i.e. they can be added to the particular aqueous ruthenium salt solution before precipitation of the ruthenium oxide hydrate. They are then added to the reaction mixture directly together with the catalyst.

The reaction mixture from the hydrogenation is typically purified.

The reaction mixture is typically purified by rectification or distillation.

The inorganic additive and the heterogeneous Ru catalyst can be removed before the distillation, for example by a solid-liquid separation, such as filtration, sedimentation or centrifugation.

Solvents and unconverted starting materials can be recycled into the process.

The cycloaliphatic amines obtainable by the process according to the invention can be used as a synthesis unit for the preparation of surfactants, pharmaceutical and crop protection compositions, stabilizers including light stabilizers, polymers, isocyanates, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerants, emulsifiers and/or as starting substances for the preparation of ureas and polyureas.

In particular, it is possible to use cyclohexylamine obtainable by the hydrogenation of aniline as a corrosion inhibitor or vulcanization accelerant. 4,4'-diaminodicyclohexylmethane, 4,4'-diamino-3,3',5,5'-tetramethyldicyclohexylmethane or 4,4'-diamino-3,3'-dimethyldicyclohexylmethane can be used as a monomer unit for polyamides, as a hardener for epoxy resins or as a starting material for the preparation of the corresponding isocyanates.

The advantages of the process according to the invention are that the process according to the invention generally has a high space time yield. In addition, the process typically ensures stable operation, since problems which occur as a result of agglomeration of catalyst particles and the resulting blockages are reduced.

The reduced sedimentation tendency of the catalyst particles generally ensures that essentially the entire amount of catalyst used is available to the reaction mixture and a portion of the catalyst is not removed by sediments.

In addition, the process according to the invention can increase the yield of product and reduce the formation of by-products, especially when starting materials which comprise a certain level of troublesome by-products are used. The process is therefore generally suitable particularly for the hydrogenation of aromatic starting materials which comprise by-products such as hydrochlorides of the aromatic starting amines or higher-boiling impurities.

The process according to the invention is therefore also generally suitable for starting materials which have a chlorine content of 1 ppm and more, or a proportion of higher-boiling products which is 1% by weight or more.

The process according to the invention is illustrated in detail by the examples which follow.

Examples 1 to 4

Examples 1 to 4 show the advantages of the present invention when using a chlorinated starting compound. Examples 1 to 4 were each carried out under the same reaction conditions.

In example 1, no inorganic additive was added.

In examples 2 to 4, in each case 5% by weight, based on the catalyst (calculated as elemental ruthenium) of inorganic additives was added. These were the following components:

Example 2 calcium stearate metal soap (particle size <200 μm)

Example 3 hydrophilic colloidal precipitated silica—spray-dried (spec. surface area approx. 190 m²/g, mean primary particle size approx. 18 nm, particle size to ISO 13320-1: 30 to 200 μm) (Sipernat® 22 from Evonik-Degussa GmbH)

Example 4 hydrophobic, colloidal, chemically aftertreated silica (spec. surface area approx. 110 m²/g, mean primary particle size approx. 28 nm) (Sipernat® D17 from Evonik-Degussa GmbH)

Procedure: Experiments 1-4

A roll autoclave with a glass insert was initially charged with 250 parts by weight of bis(4-amino-3-methylphenyl) methane, 2.5 parts by weight of catalyst suspension and if appropriate the particular amount of inorganic additive (examples 2 to 4). The catalyst suspension comprised 2% by weight, based on the suspension, of ruthenium catalyst (calculated as elemental ruthenium) and 0.134% by weight, based on the suspension, of bis(4-amino-3-methylphenyl) methane hydrochloride.

The autoclave was first flushed with gaseous nitrogen, then hydrogen was injected in the cold state until a pressure of 100 bar was established. Then the rolling operation was begun and the temperature was simultaneously increased from room temperature to 230° C. within 4 hours. Additional hydrogen was then injected until a pressure of 270 bar was established.

The roll autoclave was then operated at a temperature of 230° C. for 5 hours, in the course of which additional hydrogen was injected at hourly intervals in order to maintain the pressure of 270 bar.

Thereafter, the pressure was adjusted once again to 270 bar of hydrogen and both the rolling drive and the heating were switched off.

Once the reaction mixture had reached room temperature, the autoclave was decompressed, and the reaction mixture was removed and the catalyst and inorganic additive were filtered off.

The filtrate was then subjected to a fractional distillation under reduced pressure.

The results obtained in each case are reproduced below (concentration data in % by weight):

|  | Example 1 (comparative, without additive) | Example 2 Calcium stearate | Example 3 SiO₂ (hydrophilic) | Example 4 SiO₂ (hydrophobic) |
| --- | --- | --- | --- | --- |
| Low-boiling by-products | 1.71 | 2.38 | 2.46 | 3.0 |
| End product | 47.19 | 68.7 | 75.14 | 71.58 |
| Intermediate | 41.86 | 19.16 | 12.99 | 16.82 |
| Starting material | 0.24 | 0.16 | 0 | 0 |
| High-boiling by-products | 9.0 | 9.6 | 9.4 | 8.6 |

End product: bis(4-amino-3-methylcyclohexyl)methane

Intermediate: (4-amino-3-methylcyclohexyl)(4-amino-3-methylphenyl)methane

Starting material: bis(4-amino-3-methylphenyl)methane

In examples 2 to 4, significantly higher conversions were achieved compared to example 1.

Example 5

Example 5 demonstrates a continuous hydrogenation by the process according to the invention.

The preparation of the Ru(IV) oxide hydrate was carried out according to example 1 in DE 21 32 547, with the only exception that the final drying under reduced pressure was omitted. To prepare the catalyst suspension, 5500 g of the filtercake thus prepared (with 579 g of Ru, calculated 100%) and 280 g of hydrophobic SiO₂ (Sipernat D17® from Evonik-Degussa GmbH) were added to a stirred vessel and mixed intensively with 150 kg of a liquid product mixture (output of the hydrogenation reactor), such that the suspension obtained comprised 0.37% by weight of Ru.

The performance of the hydrogenation was performed in a continuous production plant with a cooled high-pressure bubble column reactor. 500 kg/h of a liquid melt of bis(4-aminophenyl)methane and 6.7 kg/h of the catalyst suspension were fed continuously into this reactor. The pressure in the reactor was regulated to 200 bar by replenishing pure hydrogen. The temperature in the reactor was kept constant within the range from 230 to 240° C. by cooling.

The product mixture exiting from the reactor was decompressed and cooled to a temperature of 100° C. The analysis of the product mixture by means of gas chromatography gave the following values (concentration data in % by weight):

|  | Reaction output analysis % by weight |
|---|---|
| Low-boiling by-products | 7.85 |
| High-boiling by-products | 2 |
| End product | 90 |
| Intermediate | 0.1 |
| Starting material | 0.05 |

End product: bis(4-aminocyclohexyl)methane
Intermediate: (4-aminocyclohexyl)(4-aminophenyl)methane
Starting material: bis(4-aminophenyl)methane The hydrogenation was conducted over a period of four weeks under constant conditions without any decline in the reactivity or else a blockage of the reactor as a result of solid sedimentation being observed. Without addition of the inorganic additives, sediments which disrupt production and lead to a decrease in the yield and selectivity generally occur after only one week.

The invention claimed is:

1. A process for preparing cycloaliphatic amines comprising:
    performing hydrogenation of corresponding aromatic compounds with hydrogen-comprising gas at a temperature of from 30 to 280° C. and a pressure of 50-350 bar, in the presence of ruthenium catalysts used without support material, and from 1% by weight to 500% by weight, based on the catalyst (calculated as elemental ruthenium (Ru)), of suspended inorganic additives or metal soaps, wherein the inorganic additives are selected from the group consisting of silicon dioxide, alkali metal silicates, alkaline earth metal silicates, aluminum silicates, alkali metal borosilicates, alkaline earth metal borosilicates, aluminum borosilicates, titanium dioxide, zeolites, magnesium oxide, zinc oxide, zirconium oxide, activated carbons, carbon molecular sieves, natural carbon black, and synthetic carbon black.

2. The process of claim 1, wherein the inorganic additives have a specific surface area of from 10 to 1000 m$^2$/g.

3. The process of claim 1, wherein the inorganic additives have a mean primary particle size of from 1 to 500 nm.

4. The process of claim 1, wherein the inorganic additives used are hydrophobic silicates.

5. The process of claim 1, wherein the aromatic compounds used are mono- or polycyclic aromatic amines.

6. The process of claim 1, wherein the hydrogenation is performed in continuous mode.

7. The process of claim 1, wherein the hydrogenation is performed in the presence of a solvent.

8. The process of claim 1, wherein the end product formed in the reaction is used as the solvent.

9. The process of claim 1, wherein the hydrogenation is performed in the presence of a Ru catalyst whose precursor is ruthenium oxide hydrate.

10. The process of claim 1, wherein the hydrogenation is performed in the presence of from 5% by weight to 200% by weight, based on the catalyst (calculated as elemental ruthenium) of suspended inorganic additives.

11. The process of claim 1, wherein the aromatic starting compounds used in the process have a chlorine content of 1 ppm or more and/or a content of higher-boiling aromatic by-products of 1% by weight or more.

12. The process of claim 1, wherein the aromatic compound is any one or more selected from the group consisting of: polymeric MDA, aniline, 4,4'-diamino-3,3'-dimethyldiphenylmethane, 4,4'-diamino-3,3',5,5'-tetramethyldiphenylmethane, and 4,4'-diaminodiphenylmethane.

13. A method for preparing surfactants, pharmaceutical and crop protection compositions, stabilizers including light stabilizers, polymers, isocyanates, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerants, emulsifiers and/or as starting substances for the preparation of ureas and polyureas comprising:
    preparing a cycloaliphatic amine in accordance to claim 1; and
    utilizing the cycloaliphatic amine to prepare surfactants, pharmaceutical and crop protection compositions, stabilizers including light stabilizers, polymers, isocyanates, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerants, emulsifiers and/or as starting substances for the preparation of ureas and polyureas.

14. A method for preparing a corrosion inhibitor or vulcanization accelerant comprising:
    preparing a cycloaliphatic amine in accordance to claim 12; and
    utilizing the cycloaliphatic amine to prepare the corrosion inhibitor or vulcanization accelerant.

15. A method for preparing polyamides, epoxy resins, or isocyanates comprising:
    preparing a 4,4'-diaminodicyclohexylmethane, 4,4'-diamino-3,3',5,5'-tetramethyldicyclohexylmethane or 4,4'-diamino-3,3'-dimethyldicyclohexylmethane in accordance to claim 12; and
    utilizing the 4,4'-diaminodicyclohexylmethane, tetramethyldicyclohexylmethane or 4,4'-diamino-3,3'-dimethyldicyclohexylmethane to prepare the polyamides, epoxy resins, or isocyanates.

16. A process for preparing cycloaliphatic amines comprising:
    performing hydrogenation of corresponding aromatic compounds with hydrogen-comprising gas at a temperature of from 30 to 280° C. and a pressure of 50-350 bar, in the presence of ruthenium catalysts used without support material, and from 1% by weight to 500% by weight, based on the catalyst (calculated as elemental ruthenium (Ru)), of suspended inorganic additives or metal soaps, wherein the inorganic additives are selected from the group consisting of silicon dioxide, alkali metal silicates, alkaline earth metal silicates, aluminum silicates, alkali metal borosilicates, alkaline earth metal borosilicates, aluminum borosilicates, titanium dioxide, zeolites, magnesium oxide, zinc oxide, and zirconium oxide, and wherein the inorganic additives have a specific surface area of from 10 to 1000 m$^2$/g.

17. A process for preparing cycloaliphatic amines comprising:
    performing hydrogenation of corresponding aromatic compounds with hydrogen-comprising gas at a temperature of from 30 to 280° C. and a pressure of 50-350 bar, in the presence of ruthenium catalysts used without support material, and from 1% by weight to 500% by weight, based on the catalyst (calculated as elemental ruthenium (Ru)), of suspended inorganic additives or metal soaps, wherein the inorganic additives are selected from the group consisting of silicon dioxide, alkali metal silicates, alkaline earth metal silicates, aluminum silicates, alkali metal borosilicates, alkaline earth metal borosilicates, aluminum borosilicates, titanium dioxide, zeolites, magnesium oxide, zinc oxide, and zirconium oxide, and wherein the inorganic additives have a mean primary particle size of from 1 to 500 nm.

18. The process of claim 1, wherein the cycloaliphatic amine is bis(4-amino-3-methylcyclohexyl)methane and the inorganic additive is silicon dioxide.

19. The process of claim 16, wherein the cycloaliphatic amine is bis(4-amino-3-methylcyclohexyl)methane and the inorganic additive is silicon dioxide.

20. The process of claim 17, wherein the cycloaliphatic amine is bis(4-amino-3-methylcyclohexyl)methane and the inorganic additive is silicon dioxide.

21. The process of claim 1, wherein the inorganic additives have a specific surface area of from 25 to 300 $m^2/g$.

* * * * *